United States Patent
Nagata et al.

(10) Patent No.: US 7,622,111 B2
(45) Date of Patent: Nov. 24, 2009

(54) FUSION PROTEIN OF HUMAN IGG1 HEAVY CHAIN CONSTANT REGION AND SCFV ANTIBODY AGAINST EQUINE ENCEPHALITIS VIRUS

(75) Inventors: Leslie P. Nagata, Medicine Hat (CA); R. Elaine Fulton, Medicine Hat (CA); Weigang Hu, Medicine Hat (CA); Azhar Z. Alvi, Mississauga (CA)

(73) Assignee: Her Majesty the Queen in right of Canada, as represented by the Minister of National Defence, Ontario (CA)

( * ) Notice: Subject to any disclaimer, the term of this patent is extended or adjusted under 35 U.S.C. 154(b) by 1144 days.

(21) Appl. No.: 10/378,832

(22) Filed: Mar. 5, 2003

(65) Prior Publication Data

US 2004/0005333 A1    Jan. 8, 2004

(51) Int. Cl.
  A61K 39/42    (2006.01)
(52) U.S. Cl. .............. 424/133.1; 424/135.1; 424/159.1
(58) Field of Classification Search ........................ None
  See application file for complete search history.

(56) References Cited

OTHER PUBLICATIONS

Alvi et al., "Development of a Functional Monoclonal Single-Chain Variable Fragment Antibody Against Venezuelan Equine Encephalitis Virus," Hybridoma, vol. 18, No. 5, pp. 413-421, Mary Ann Liebert Inc. (1999).

Long et al., "Construction and Characterization of a Novel Recombinant Single-Chain Variable Fragment Antibody Against Western Equine Encephalitis Virus," Hybridoma, vol. 19, No. 1, pp. 1-13, Mary Ann Liebert Inc. (2000).

Roehrig et al., "Use of a New Synthetic-Peptide-Derived Monoclonal Antibody to Differentiate Between Vaccine and Wild-Type Venezuelan Equine Encephalomyelitis Viruses," Journal of Clinical Microbiology, vol. 29, No. 3, pp. 630-631 American Society for Microbiology, (1991).

Roehrig et al., "Antigenic Analysis of the Surface Glycoproteins of a Venezuelan Equine Encephalomyelitis Virus (TC-83) Using Monoclonal Antibodies," Virology, vol. 118, pp. 269-278 Academic Press Inc. (1982).

Roehrig et al., "The Neutralization Site on the E2 Gylcoprotein of Venezuelan Equine Encphalomyelitis (TC-83) Virus is Composed of Multiple Conformationally Stable Epitopes," Virology, vol. 142, pp. 347-356, Academic Press Inc. (1985).

Alvi et al., "Functional Enhancement of a Partially Active Single-Chain Variable Fragment Antibody to Venezuelan Equine Encephalitis Virus," Viral Immunology, vol. 16, No. 2, pp. 213-222, Mary Ann Liebert Inc. (2003).

Alvi, A.Z., Stadnyk, L.L., Nagata, L.P., Fulton, R.E., Bader, D.E., Roehrig, J.T. and Suresh, M.R., *Development of a Functional Monoclonal Single-Chain Variable Fragment Antibody Against Venezuelan Equine Encephalitis Virus*, Hybridoma, vol. 18, No. 5, 413-421, (1999).

Long, M.C., Jager, S., Mah, D.C., Jebailey, L., Mah, M.A., Masri, S.A. and Nagata, L.P., *Construction and Characterization of a Novel Recombinant Single-Chain Variable Fragment Antibody Against Western Equine Encephalitis Virus*, Hybridoma, vol. 19, No. 1, 1-13, (2000).

Xu, B., Kriangkum, J., Nagata, L.P., Fulton, R.E. and Suresh, M.R., *A Single Chain Fv Specific Against Western Equine Encephalitis Virus*, Hybridoma, 18, 315-323, (1999).

*Primary Examiner*—Stacy B Chen
(74) *Attorney, Agent, or Firm*—Rader, Fishman & Grauer, PLLC

(57) ABSTRACT

Construction of a recombinant gene fusion encoding a human IgG1 heavy chain constant region and a single-chain variable fragment antibody of 1A4A1 monoclonal antibody is disclosed. The recombinant antibody of the present invention confers human immune effector functions on murine antibodies. After expression in bacteria as inclusion bodies, the recombinant antibody was purified and refolded in vitro. The recombinant soluble antibody retains high antigen-binding affinity to VEE and possesses some human IgG crystallizable fragment domain functions. On non-reducing gel electrophoresis analysis, disulfide bond formation was found in the hinge region of the recombinant antibody. The present invention shows that the recombinant antibody is in a native, functionally active form and it provides the basis to characterize the recombinant antibody for efficacy in vivo.

15 Claims, 9 Drawing Sheets

FIGURE 2

```
                                6His                                              Xpress epitope
   1  ATGCGGGGTTCTCATCATCATCATCATCATGGTATGGCTAGCATGACTGGTGGACAGCAAATGGGTCGGGATCTGTACGACGATGACGAT
   1▶ M  R  G  S  H  H  H  H  H  H  G  M  A  S  M  T  G  G  Q  Q  M  G  R  D  L  Y  D  D  D  D
           Enterokinase cleavage site
  91  AAGGATCGATGGGGATCCCAGCTCGAGATCTGCAGCTGGTACCATGGAATTCCTTTAGTTGTTCCTTTCTATGCGGCCCAGCCGGCCATG
  31▶ K  D  R  W  G  S  E  L  E  I  C  S  W  Y  H  G  I  P  L  V  V  P  F  Y  A  A  Q  P  A  M 181  GCCCAGGTCCAACTGCAGGAGTCAGGACCTGAGCTGGTGAAGCCTGGGGCTTCAGTGAAGATATCCTGCAAGGCCTCTGGCTACACCTTC
  61▶ A  Q  V  Q  L  Q  E  S  G  P  E  L  V  K  P  G  A  S  V  K  I  S  C  K  A  S  G  Y  T  F
         VH CDR1                                                                  VH CDR2
 271  ACTGACTACCATGTTCACTGGGTGAAGGGGAAGCCTGGACAGGGACTTGAATGGATTGGAATGACTTATCCTGGATTCGATAATACTAAT
  91▶ T  D  Y  H  V  H  W  V  K  G  K  P  G  Q  G  L  E  W  I  G  M  T  Y  P  G  F  D  N  T  N 361  TACAGTGAGACTTTCAAGGGCAAGGCCACATTGACTGTAGACACATCCTCCAACACAGTCTACATGCAGCTCAGCAGCCTGACATCTGAG
 121▶ Y  S  E  T  F  K  G  K  A  T  L  T  V  D  T  S  S  N  T  V  Y  M  Q  L  S  S  L  T  S  E
                              VH CDR3
 451  GACACCGCTGTCTATTTTTGTGCAAGAGGTGTGGGCCTTGACTACTGGGGCCAAGGGACCACGGTCACCGTCTCCTCAGGTGGAGGCGGT
 151▶ D  T  A  V  Y  F  C  A  R  G  V  G  L  D  Y  W  G  Q  G  T  T  V  T  V  S  S  G  G  G  G
            Linker
 541  TCAGGCGGAGGTGGCTCTGGCGGTGGCGGATCGGACATCGAGCTCACTCAGTCTCCAAATTCGTTGTCCACATCAATAGGAGACAGGATC
 181▶ S  G  G  G  G  S  G  G  G  S  D  I  E  L  T  Q  S  P  N  S  L  S  T  S  I  G  D  R  I
                                                   VL CDR1
 631  AGAATCACCTGCAAGGCCAGTCAGGATGTGGATACTGCTGTAGGCTGGTATCAACAGAGACCAGGGCAATCTCCTAAACTACTGATTTTC
 211▶ R  I  T  C  K  A  S  Q  D  V  D  T  A  V  G  W  Y  Q  Q  R  P  G  Q  S  P  K  L  L  I  F
             VL CDR2
 721  TGGTCATCCACCCGGCACACTGGAGTCCCTGATCGCTTCACAGGCAGTGGATCTGGGACAGATTTCACTCTCACCATTAGCAATGTGCAG
 241▶ W  S  S  T  R  H  T  G  V  P  D  R  F  T  G  S  G  S  G  T  D  F  T  L  T  I  S  N  V  Q
                                                     VL CDR3
 811  TCTGAAGACTTGGCAGATTATTTCTGTCACCAATATAGCAGCTATCCATTCACGTTCGGCTCGGGGACAAAGTTGGAAATAAAACGGGCG
 271▶ S  E  D  L  A  D  Y  F  C  H  Q  Y  S  S  Y  P  F  T  F  G  S  G  T  K  L  E  I  K  R  A 901  GCCGCGGCCTGCCTGGTCAAGGACTACTTCCCCGAACCGGTGACGGTGTCGTGGAACTCAGGCGCCCTGACCAGCGGCGTGCACACCTTC
 301▶ A  A  G  C  L  V  K  D  Y  F  P  E  P  V  T  V  S  W  N  S  G  A  L  T  S  G  V  H  T  F
                                                      CH1
 991  CCGGCTGTCCTACAGTCCTCAGGACTCTACTCCCTCAGCAGCGTGGTGACCGTGCCCTCCAGCAGCTTGGGCACCCAGACCTACATCTGC
 331▶ P  A  V  L  Q  S  S  G  L  Y  S  L  S  S  V  V  T  V  P  S  S  S  L  G  T  Q  T  Y  I  C
                                                                                        Hinge
1081  AACGTGAATCACAAGCCCAGCAACACCAAGGTGGACAAGAGAGTTGAGCCCAAATCTTGTGACAAAACTCACACATGCCCACCGTGCCCA
 361▶ N  V  N  H  K  P  S  N  T  K  V  D  K  R  V  E  P  K  S  C  D  K  T  H  T  C  P  P  C  P 1171  GCACCTGAACTCCTGGGGGGACCGTCAGTCTTCCTCTTCCCCCCAAAACCCAAGGACACCCTCATGATCTCCCGGACCCCTGAGGTCACA
 391▶ A  P  E  L  L  G  G  P  S  V  F  L  F  P  P  K  P  K  D  T  L  M  I  S  R  T  P  E  V  T 1261  TGCGTGGTGGTGGACGTGAGCCACGAAGACCCTGAGGTCAAGTTCAACTGGTACGTGGACGGCGTGGAGGTGCATAATGCCAAGACAAAG
 421▶ C  V  V  V  D  V  S  H  E  D  P  E  V  K  F  N  W  Y  V  D  G  V  E  V  H  N  A  K  T  K
                                                      CH2
1351  CCGCGGGAGGAGCAGTACAACAGCACGTACCGTGTGGTCAGCGTCCTCACCGTCCTGCACCAGGACTGGCTGAATGGCAAGGAGTACAAG
 451▶ P  R  E  E  Q  Y  N  S  T  Y  R  V  V  S  V  L  T  V  L  H  Q  D  W  L  N  G  K  E  Y  K 1441  TGCAAGGTCTCCAACAAAGCCCTCCCAGCCCCCATCGAGAAAACCATCTCCAAAGCCAAAGGCAGCCCCGAGAACCACAGGTGTACACC
 481▶ C  K  V  S  N  K  A  L  P  A  P  I  E  K  T  I  S  K  A  K  G  Q  P  R  E  P  Q  V  Y  T 1531  CTGCCCCCATCCCGGGATGAGCTGACCAAGAACCAGGTCAGCCTGACCTGCCTGGTCAAAGGCTTCTATCCCAGCGACATCGCCGTGGAG
 511▶ L  P  P  S  R  D  E  L  T  K  N  Q  V  S  L  T  C  L  V  K  G  F  Y  P  S  D  I  A  V  E
                                                      CH3
1621  TGGGAGAGCAATGGGCAGCCGGAGAACAACTACAAGACCACGCCTCCCGTGCTGGACTCCGACGGCTCCTTCTTCCTCTACAGCAAGCTC
 541▶ W  E  S  N  G  Q  P  E  N  N  Y  K  T  T  P  P  V  L  D  S  D  G  S  F  F  L  Y  S  K  L 1711  ACCGTGGACAAGAGCAGGTGGCAGCAGGGGAACGTCTTCTCATGCTCCGTGATGCATGAGGCTCTGCACAACCACTACACGCAGAAAAGC
 571▶ T  V  D  K  S  R  W  Q  Q  G  N  V  F  S  C  S  V  M  H  E  A  L  H  N  H  Y  T  Q  K  S 1801  TTGATCCGGCTGCTAACAAAGCCCGAAAGGAAGCTGAGTTGGCTGCTGCCACCGCTGAGCAATAACTAG
 601▶ L  I  R  L  L  T  K  P  E  R  K  L  S  W  L  L  P  P  L  S  N  N
```

FIGURE 6A

FUSION PROTEIN OF HUMAN IGG1 HEAVY CHAIN CONSTANT REGION AND SCFV ANTIBODY AGAINST EQUINE ENCEPHALITIS VIRUS

FIELD OF THE INVENTION

This invention relates to the construction of a recombinant gene fusion encoding a human IgG1 heavy chain constant region and a single-chain variable fragment antibody of 1A4A1 monoclonal antibody.

BACKGROUND OF THE INVENTION

List of Prior Art Literatures

1. Adams, G. P., Schier, R., McCall, A. M., Crawford, R. S., Wolf, E. J., Weiner, L. M. and Marks, J. D. (1998) *Br. J. Cancer.*, 77,1405-1412.
2. Alvi, A. Z., Stadnyk, L. L., Nagata, L. P., Fulton, R. E., Bader, D. E., Roehrig, J. T. and Suresh, M. R. (1999) *Hybridoma*, 18, 413-421.
3. Boleti, E., Deonarain, M. P., Spooner, R. A., Smith, A. J., Epenetos, A. A. and George, A. J. (1995) *Ann. Oncol.*, 6, 945-947.
4. Breedveld, F. C. (2000) *Lancet*, 355, 735-740.
5. Burton, D. R. (1985) *Mol. Immunol.*, 22, 161-206.
6. Calisher, C. H. (1994) *Clin. Microbiol. Rev.*, 7, 89-116.
7. Colcher, D., Bird, R., Roselli, M., Hardman, K. D., Johnson, S., Pope, S., Dodd, S. W., Pantoliano, M. W., Milenic, D. E. and Schlom, J. (1990) *J. Natl. Cancer. Inst.*, 82,1191-1197.
8. Colcher, D., Pavlinkova, G., Beresford, G., Booth, B. J., Choudhury, A. and Batra, S. K. (1998) *Q. J. Nucl. Med.*, 42, 225-241.
9. Eshhar, Z., Waks, T., Gross, G. and Schindler, D. G. (1993) *Proc. Natl. Acad. Sci. USA*, 90, 720-724.
10. France, J. K., Wyrick, B. C. and Trent, D. W. (1979) *J. Gen. Virol.*,44,725-740.
11. Franck, P. T. and Johnson, K. M. (1970) *Am. J. Trop. Med. Hyg.*, 19, 860-865.
12. George, A. J., Jamar, F., Tai, M. S., Heelan, B. T., Adams, G. P., McCartney, J. E., Houston, L. L., Weiner, L. M., Oppermann, H. and Peters, A. M. (1995) *Proc. Natl. Acad. Sci. USA*, 92, 8358-8362.
13. Groot, H. (1972) *In: Venezuelan encephalitis, Scientific publication no. 243. The health and economic importance of Venezuelan equine encephalitis (VEE).* Pan America Health Organization, Washington D.C. Pp. 7-16.
14. Harlow, E. D. and D, Lane. (1999) *Using Antibodies: a laboratory manual. Immunoprecipitation.* $1^{st}$ ed. Cold Spring Harbor Laboratory Press, Cold Spring Harbor, N.Y.
15. Hughes-Jones, N. C. and Gardner, B. (1979) *Mol. Immunol.*,16, 697-701.
16. Jahrling, P. B. and Stephenson, E. H. (1984) *J. Clin. Microbiol.*,19, 429-431.
17. Johnson, K. M., Shelokov, A., Peralta, P. H., Dammin, G. J. and Young, N. A. (1968) *Am. J. Trop. Med. Hyg.*, 17, 432-440.
18. Johnson, K. M. and Martin, D. H. (1974) *Adv. Vet. Sci. Comp. Med.*, 18, 79-116.
19. Johnston, R. E. and Peters, C. J. (1996) In Fields, B. N., Knipe, D. M. and Honley, P. M. (eds.), *Fields virology. Alphaviruses.* $3^{rd}$ ed. Raven Publishers, Philadelphia, Pa. pp.843-898.
20. Kuroki, M., Arakawa, F., Khare, P. D., Kuroki, M., Liao, S., Matsumoto, H., Abe, H. and Imakiire, T. (2000) *Anticancer Res.*, 20, 4067-4071.
21. Leatherbarrow, R. J., Rademacher, T. W., Dwek, R. A., Woof, J. M., Clark, A., Burton, D. R., Richardson, N. and Feinstein, A. (1985) *Mol. Immunol.*, 22, 407-415.
22. Long, M. C., Jager, S., Mah, D. C., Jebailey, L., Mah, M. A., Masri, S. A. and Nagata, L. P. (2000) *Hybridoma*, 19, 1-13.
23. McGregor, D. P., Molloy, P. E., Cunningham, C. and Harris, W. J. (1994) *Mol. Immunol.*, 31, 219-226.
24. Milenic, D. E., Yokota, T., Filpula, D. R., Finkelman, M. A., Dodd, S. W., Wood, J. F., Whitlow, M., Snoy, P. and Schlom, J. (1991) *Cancer. Res.*, 51, 6363-6371.
25. Nose, M. and Wigzell, H.(1983) *Proc. Natl. Acad. Sci. USA*, 80,6632-6636.
26. Pittman, P. R., Makuch, R. S., Mangiafico, J. A., Cannon, T. L., Gibbs, P. H. and Peters, C. J. (1996) *Vaccine*, 14, 337-343.
27. Roehrig, J. T., Day, J. W. and Kinney, R. M. (1982) *Virology*, 118, 269-278.
28. Roehrig, J. T. and Mathews, J. H. (1985) *Virology,*142, 347-356.
29. Roehrig, J. T., Bolin, R. A., Hunt, A. R. and Woodward, T. M. (1991) *J. Clin. Microbiol.*, 29, 630-631.
30. Schlesinger, S. and Schlesinger, M. J. (1996) In Fields, B. N., Knipe, D. M. and Honley, P. M. (eds.), *Fields virology. Togaviridae: The viruses and their replication.* $3^{rd}$ ed. Raven Publishers, Philadelphia, Pa. pp.825-841.
31. Schroff, R. W., Foon, K. A., Beatty, S. M., Oldham, R. K. and Morgan, A. C. Jr. (1985) *Cancer Res.*, 45, 879-885.
32. Stone, G. C., Sjobring, U., Bjorck, L., Sjoquist, J., Barber, C. V. and Nardella, F. A. (1989) *J. Immunol.*,143, 565-570.
33. Sutton B J, Phillips D C. (1983) *Biochem Soc Trans.* 11 Pt 2,130-2.
34. Tao, M. H. and Morrison, S. L. (1989) *J. Immunol.*,143, 2595-2601.
35. Verma, R., Boleti, E. and George, A. J. (1998) *J. Immunol. Methods*, 216, 165-181.
36. Walton, T. E. and Grayson, M. A. (1988) In Monath, T. P. (ed.), *Venezuelan equine encephalomyelitis. The Arboviruses: Epidemiology and Ecology*, vol. IV. CRC press, Boca Raton, Fla. pp.203-233.
37. Wels, W., Harwerth, I. M., Mueller, M., Groner, B. and Hynes, N. E. (1992) *Cancer Res.*,52, 6310-6317.
38. Winter, G. and Milstein, C. (1991) *Nature*, 349, 293-299.
39. Xu, B., Kriangkum, J., Nagata, L. P., Fulton, R. E. and Suresh, M. R. (1999) *Hybridoma*, 18, 315-323.

Venezuelan equine encephalitis virus (VEE), a member of alphavirus genus of the family Togaviridae, is an important pathogen of epidemic diseases in humans and of epizootics in rodents, horses, donkeys, and mules in the Americas (Johnston and Peters, 1996). VEE causes a spectrum of human diseases ranging from subclinical infection to acute encephalitis (Franck and Johnson, 1970; Johnson et al., 1968). Neurological disease appears in four to 14% of cases (Johnson and Martin, 1974; Walton and Grayson, 1988). The incidence of human infection during equine epizootics could be up to 30% (Groot, 1972). VEE is a potential biological warfare agent of concern. However, there are no antiviral drugs available that are effective against VEE. Although live-attenuated and inactivated vaccines against VEE have been developed, these products are far from satisfactory. Approximately 20% of live-attenuated TC-83 vaccine recipients fail to develop neutralizing antibodies (Abs), while another 20% exhibit reactogenicity (Pittman et al., 1996). A formaldehyde-inactivated vaccine, C-84, is well tolerated, but requires multiple immunization, periodic boosts, and fails to provide protection against aerosol challenge in some rodent models (Jahrling and Stephenson, 1984).

VEE complex is a group of antigenically related, but distinct, viruses divided into six subtypes (Calisher, 1994). VEE virions are composed of an icosahedral nucleocapsid, which is surrounded by a lipid envelope containing two structural glycoproteins, E1 and E2 (Schlesinger and Schlesinger, 1996). Epitopes on E1 and E2 are the targets of neutralizing Abs. Studies have shown that the viral neutralizing epitopes are mainly located on the E2 protein, and that the $E2^C$ epitope appears to be the hub of the neutralization epitopes (France et al., 1979; Roehrig et al., 1982; Roehrig et al., 1991; Roehrig and Mathews, 1985). Monoclonal antibody (MAb) 1A4A1 is specific for $E2^C$. This MAb has been shown to be efficient in protecting animals from a lethal peripheral challenge with virulent VEE (Roehrig and Mathews, 1985).

Murine MAbs, however, have serious disadvantages as therapeutic agents in humans (Breedveld, 2000; Schroff et al., 1985). They induce human anti-mouse antibodies (HAMA). Re-treatment may result in rapid clearance of the murine MAbs and anaphylaxis. Limitations in the use of murine MAbs in clinical applications led to the development of single-chain variable fragment (scFv) Abs (Winter, 1991). ScFv Abs have several advantages compared with the mouse parental MAbs from which they are generated. They generally retain the same specificity and similar affinity to antigens (Kuroki et al., 2000), and demonstrate decreased immunogenicity as compared with the parental mouse MAbs (Colcher et al., 1998). Furthermore, scFv Abs can be produced economically and in a short period of time in bacteria or yeast (McGregor et al., 1994; Verma et al., 1998), and can be manipulated by genetic engineering to form novel proteins by fusion with other molecules, such as metal-binding proteins (George et al., 1995), cytokines (Boleti et al., 1995), toxins (Wels et al., 1992), or T cell receptors (Eshhar et al., 1993). Although scFvs have immense potential in immunodiagnostics (Colcher et al., 1990; Milenic et al., 1991), they have limited utility in immunotherapy, probably due to their monovalent nature, size and the fact that they are rapidly cleared from body circulation. Furthermore, they are unable to recruit effector functions due to the lack of an Ab constant region.

The present inventors have cloned and characterized several scFv Abs against the alphavirus genus, VEE or Western equine encephalitis virus (WEE) (Alvi et al., 1999; Long et al., 2000; Xu et al., 1999). An anti-VEE A116 scFv Ab was cloned from 1A4A1 MAb, as disclosed by the Applicant in U.S. patent application Ser. No. 10/096,246, herein incorporated by reference. However, in vitro binding assays indicated that A116 scFv Ab had low binding affinity to VEE, in comparison to the parental MAb. Sequence analysis of A116 revealed that three bases were missing in the conserved framework-1 region of the variable region of the light chain ($V_L$). Polymerase chain reaction-based site-directed mutagenesis was used to introduce the three missing bases, resulting in a repaired A116 scFv Ab, designated mA116 scFv Ab, as disclosed in the same U.S. patent application Ser. No. 10/096,246. This repaired scFv showed an affinity to VEE comparable to that of the parental 1A4A1 MAb.

Antibodies have been recognized as one of the most critical components of the immune system. Many infectious diseases can be cured or prevented by specific Abs. All Abs share the same basic structure. The N-terminal domains of heavy and light chains constitute the variable regions that form the antigen-binding site. The other domains, which comprise the constant region, contribute to the activation of host effector functions such as complement activation, stimulation of phagocytosis by macrophages, and antibody-dependent cellular cytotoxicity (ADCC) (Breedveld, 2000). These effector functions are often required for therapeutic efficacy.

Antiviral immunity is complex, with several factors involved, such as Ab response, cell-mediated immunity, and induction of interferon. Ab response to viruses includes not only neutralization of infectivity for susceptible host cells, but also host effector functions such as complement-mediated lysis of infected host cells and opsonization. The host effector functions of Abs are attributable to the crystallizable fragment (Fc) Ab regions (Breedveld, 2000). ScFv Abs lack the Fc region, and thus lack effector functions.

Accordingly, it is desirable to produce recombinant scFv Abs having the constant region of human Abs with enhanced effector functions against VEE.

SUMMARY OF THE INVENTION

In the present invention, the inventors have genetically joined a human IgG 1 heavy chain constant region to anti-VEE mA116 scFv Ab, resulting in mA116huFc Ab. An object of the present invention is to confer on the ScFv Ab some of the human-associated effector functions without increasing immunogenicity in humans. The mA116huFc Ab gene was expressed in *E. coli* and refolded in vitro and the resulting product was purified and characterized.

Another object of the present invention is to produce mA116huFc Abs which retain antigen-binding affinity to VEE and possess some human IgG1 Fc domain functions, such as protein G and human C1q binding.

According to the present invention, it provides an expressed protein mA116huFc Ab constructed from recombinant gene fusion which comprises encoding a human IgG1 heavy chain constant region and a single-chain variable fragment ("scFv") antibody of 1A4A1 monoclonal antibody.

BRIEF DESCRIPTION OF THE DRAWINGS

FIG. 2 shows the DNA sequence (SEQ ID NO. 1) and translated amino acid sequence (SEQ ID NO. 2) of the mA116huFc Ab.

DETAILED DESCRIPTION OF THE INVENTION

Materials and Methods

Construction of pRSmA116huFc

Figure 1:
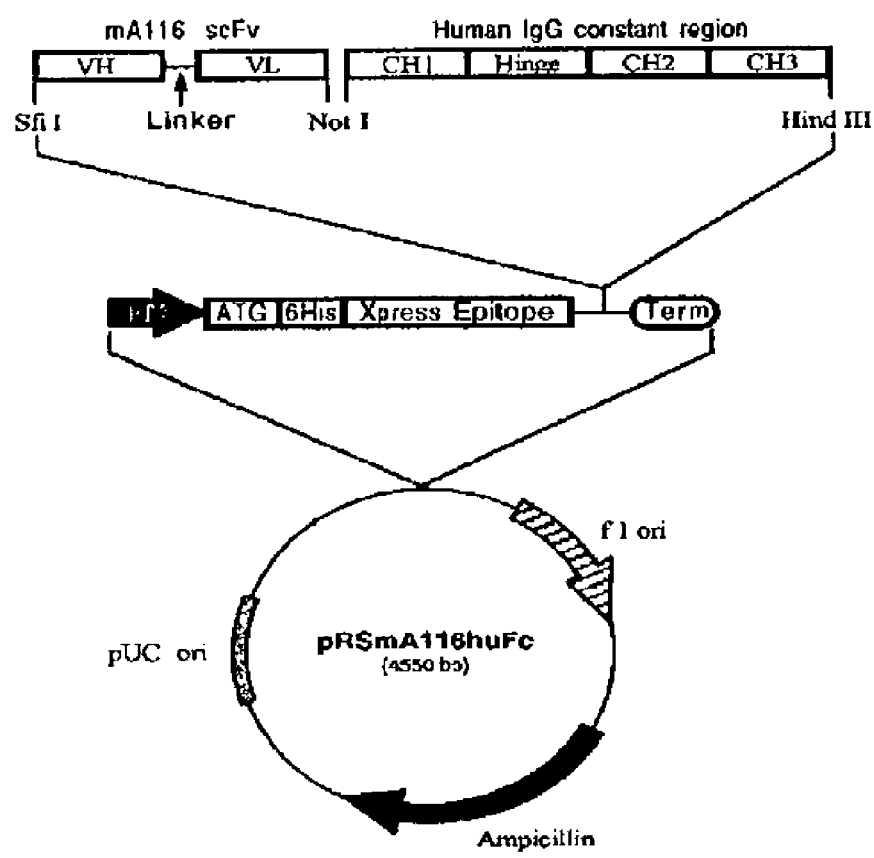
FIG. 1 shows pRSmA116huFc construct. MA 116 scFv Ab gene was cloned into the Sfi I and Not I sites of pRS10B5huFc to replace 10B5 scFv Ab gene as described under "Materials and Methods".

MA116 scFv Ab gene was derived from A116 scFv Ab gene, which was constructed using the Recombinant Phage Antibody System (Amersham Pharmacia Biotech, Baie d'Urfe', QC), as disclosed in the U.S. patent application Ser. No. 10/096,246. MA116 scFv Ab DNA fragment was separated from vector pCANTAB5E by restriction enzyme digestions with Sfi I/Not I, followed by gel electrophoresis and purification with the gel extraction kit (Qiagen, Chatsworth, Calif.). The fragment was subcloned into the Sfi I/Not I site of the pRS10B5huFc expression vector (Long et al., 2000), replacing the anti-WEE virus 10B5 scFv Ab gene. The fragment was inserted in frame with the 5' end of a gene sequence encoding a 35.8-kDa human IgG1 constant region and the 3' end of a fragment containing 6-His tag and Xpress epitope, added for ease of purification and detection. The construct was named pRSmA116huFc (FIG. 1). The recombinant plasmid DNA was transferred into Escherichia coli (E. coli) BL-21 (DE3) pLys S competent cells, containing a genomic source of T7 RNA polymerase under lacUV5 promoter control (Invitrogen, Carlsbad, Calif.). The recombinant plasmid, containing the mA116 scFv Ab gene insert, was confirmed by restriction digestion and DNA sequencing. Six primers for DNA sequencing were made on an Oligo 1000 DNA synthesizer (Beckman Instruments, Fullerton, Calif.) and were as follows: SC-1 (5'-CATCATCATCATCATCAT-3') (SEQ ID NO. 3), SC-9 (5'-CAGCAGCCAACTCAGCTT-3') (SEQ ID NO. 4), SC-13 (5'-ACTCCTGACATCCTGTCG-3') (SEQ ID NO. 5), HL-2 (5'-TCTAACGGGACCAGAGACAAC-3') (SEQ ID NO. 6), HL-3 (5'-GGTAAGTTCAGGGACAGG-3') (SEQ ID NO. 7), HU-4 (5'-TGCAAGGCCAGTCAGGATGTG-3') (SEQ ID NO. 8). Sequencing reactions were performed using a Big Dye Terminator™ cycle sequencing kit (PE Biosystems, Mississauga, ON). The reaction products were purified by Centri-Sep™ columns (Princeton Separations, Adelphia, N.J), and then run on an ABI 310 genetic analyzer system (Applied Biosystem, Fullerton, Calif.). Sequences were assembled and analyzed using Lasegene DNA software (DNA star, Madison, Wis.).

Expression Purification and Refolding of the Recombinant mA116huFc Ab

Recombinant protein, expressed in *E. coli* as inclusion bodies, was solubilized, purified, and refolded, as previously described, with minor modification (Long et al., 2000). Briefly, after induction for 3 hr by isopropyl β-D-thiogal actopyranoside (IPTG), *E. coli* transformants harboring the pRSmA116huFc expression plasmid were harvested by centrifugation. The cell pellet was resuspended in 5 mM borate sodium, pH 9.3, and 4 M urea, and cell lysate was prepared by sonication (three cycles of 10 sec; amplitude 10 μm; 15 sec cooling on ice), using a MSE Soniprep 150-probe sonicator (Wolf Laboratories, Pocklington, UK). The sonicates were centrifuged (13,000 g for 10 min) and pellets were resuspended in 5 mM borate sodium, pH 9.3, 8 mM urea, and 100 mM sodium chloride. Purification of the recombinant protein was performed on Talon™ metal affinity resin (Clontech, Palo Alto, Calif.). The solution of 5 mM borate sodium, pH 9.3, 8 M urea, and 100 mM sodium chloride was used as wash buffer. Bound fractions were eluted with 10-250 mM imidazole and 1 M arginine (final concentration) was added as cosolvent to encourage the correct folding of the protein molecules. The recombinant protein was refolded by removal of 8 M urea, by dialyzing against 5 mM borate sodium, pH 9.3, and 1 M arginine; the cosolvent was then removed by dialyzing against 5 mM borate sodium, pH 9.3. The purity was checked by sodium dodcyl sulfate-polyacrylamide gel electrophoresis (SDS-PAGE) and Coomassie brilliant blue R-250 (Bio-Rad Laboratories, Mississauga, ON) staining after concentration by ultrafiltration using Centricon™ YM-30 (Millipore Corp., Bedford, Mass.).

SDS-PAGE and Western Blot Analysis

Protein samples were electrophoresed in 10% SDS-PAGE gels, on a Mini Protein II apparatus (Bio-Rad Laboratories), under reducing (5% 2-mercaptoethanol) or non-reducing conditions. The bands were visualized by Coomassie blue staining.

The separated proteins were also transferred to Immunobilon-P membranes (Millipore Corp, Bedford, Mass.) by use of a Western blot semi-dry transfer apparatus (Bio-Rad Laboratories) with Towbin buffer (25 mM Tris-HCl, pH 8.3, 192 mM glycine, and 20% methanol). Unreacted sites were blocked with blocking buffer (3% non-fat skim milk in phosphate-buffered saline (PBS)). Blots were washed three times for 5 min with PBS containing 0.1% tween-20 (PBST). Some blots were then incubated for 1 hr at room temperature with a 1:5000 dilution of anti-Xpress Ab (Invitrogen). These blots were then washed three times for 5 min with PBST and incubated for 1 hr at room temperature with a 1:3000 dilution of horseradish peroxidase (HRP)-conjugated goat anti-mouse Ig (Caltag Laboratories, Burlingame, Calif.) in TBST. Other blots were incubated directly with either a 1:2000 dilution of HRP-conjugated donkey anti-human Ig (Jackson ImmunoResearch Laboratories, West Grove, Pa.) or a 1:1000 dilution of HRP-conjugated Ni-nitrilotriacetic acid (NTA) (Qiagen, Valencia, Calif.) at room temperature for 1 hr. After three washes for 5 min with PBST, and two washes for 2 min with deionized water, the specific binding was detected by an enhanced chemilumeniscence kit (Amersham Pharmacia Biotech).

ELISA

The reactivity of purified mA116huFc Ab to VEE antigen was determined by an enzyme-linked immunosorbent assay (ELISA). Nunc maxisorp™ flat-bottomed 96-well plates (Canadian Life Technologies, Burlington, ON) were coated overnight at 4° C. with inactivated, whole VEE (strain TC-83)

at a fixed concentration of 10 µg/ml, or various concentrations of 0.01-100 µg/ml, in carbonate bicarbonate buffer, pH 9.6, containing 0.02% sodium azide. The plates were washed five times with PBST and then blocked twice in 2% bovine serum albumin for 1 hr at 37° C. After five washes with PBST, plates were incubated for 1 hr at 37° C. with various concentrations of 0.01-100 µg/ml, or a fixed concentration of 10 µg/ml of purified Ab (mA116huFc Ab, 1A4A1 MAb, or mA116 scFv Ab) diluted in PBST. Following five washes with PBST, plates were incubated for 1 hr at 37° C. with HRP-conjugated Ab diluted 1:3000 in PBST (HRP-donkeyanti-human Ig for detection of mA116huFc Ab, HRP-goat anti-mouse Ig for 1A4A1 MAb, or HRP-anti-E tag for mA116 scFv Ab). Finally, the plates were washed five times with PBST and developed for 30 min at room temperature with a substrate consisting of 2,2'-azino-di-(3-ethyl-benzthiazoline-sulfonic acid) diammonium salt (ABTS) and hydrogen peroxidate (Kirkegaard and Perry Laboratories, Gathersburg, Md.). The reactions were read at an absorbance of 405 nm by a microplate autoreader (Molecular Devices, Sunnyvale, Calif.).

Protein G Binding Assay

The assay for purified recombinant mA116huFc Ab to bind to Protein G was modified based on an immunoprecipitation protocol (Harlow and Lane, 1999). MA116huFc Ab, 1A4A1 MAb, or mA116 scFv Ab, respectively, was incubated with washed protein G agarose (Life Technologies, Burlington, ON) in radioimmunoprecipitation (RIP) buffer (50 mM Tris-HCl, pH 7.4, 150 mM sodium chloride, 0.1% SDS, and 1% Triton X-100). After 1 hr incubation with rocking at room temperature, the agarose was collected by centrifugation at 13,000 g for 1 min at room temperature. The pellets were washed three times with RIP buffer and centrifuged at 13,000 g for 1 min. The protein G binding complexes were resuspended in Laemmli sample buffer containing 5% 2-mercaptoethanol, and heated in boiling water for 10 min. After centrifugation, the supernatants were run on a 10% SDS-PAGE gel followed by Coomassie blue staining.

Human C1q Binding Assay

The capacity of purified recombinant mA116huFc Ab to bind to human C1q was assayed using the circulating immune complexes (CIC)-C1q test kit (QUIDEL Corp., San Diego, Calif.) in accordance with the manufacturer's instructions. In brief, eight-well strips coated with human C1q protein were rehydrated by wash buffer (0.05% tween-20 and 0.01% thimerosal in PBS). The purified recombinant mA116huFc Ab, or mA116 scFv Ab, was serially diluted from 100 µg/ml in wash buffer, and incubated in the strips for 1 hr at room temperature. After five washes with wash buffer, HRP-conjugated goat anti-human Ab was added to each well and the strips were incubated at room temperature for 30 min, after which the strips were washed five times with wash buffer and incubated with ABTS substrate solution for 30 min. To stop the enzymatic reaction, stop solution containing 250 mM oxalic acid was added to the wells, and the absorbance was measured at 405 nm by the microplate autoreader.

Results

Construction, Expression and Purification

The pRS10B5huFc gene construct, in which the anti-WEE 10B5 scFv Ab gene was linked with human IgG1 heavy chain constant region (Long et al., 2000), and the anti-VEE mA116 scFv Ab gene in pCANTAB5E, were used as source materials to create the mA116huFc Ab gene construct. The 10B5 scFv Ab gene of pRS10B5huFc was replaced by the mA116scFv Ab gene. The resulting plasmid, designated pRSmA116huFc, contained the mA116scFv Ab gene, arranged in variable heavy ($V_H$)-$V_L$ chain orientation via a $(Gly_4Ser)_3$ linker, followed by human IgG1 heavy chain constant (CH) regions under the control of T7 promoter (FIG. 1). In addition, there was a 6-His tag sequence for immobilized metal affinity chromatography (IMAC) purification and a Xpress epitope for detection by anti-Xpress Ab.

The DNA sequence and translated amino acid sequence are showed in FIG. 2. The mA116 scFv Ab gene was 723 bp in length, encoding 241 residues with a molecular weight of 25.7 kDa. The frameworks for VH and VL were well-conserved, as compared with those of mouse anti-guinea pig C5 scFv Ab (Genbank AJ250760), anti-solamargine scFv Ab (Genbank AF332008), and anti-CD30 Ki-3 scFv Ab (Genbank AF280760) (data not shown). The complementarity determining region (CDR) sequences of both VH and VL were different from those of the above-noted scFv Abs (data not shown). Overall, mA116 scFv Ab was 72%, 72%, and 70% homologous to mouse anti-guinea pig C5 scFv Ab, anti-solamargine scFv Ab, and anti-CD30 Ki-3 scFv Ab, respectively. The first 66 bases of CH1 were missing from the human IgG1 CH region. The encoded Fc protein was 322 residues with a molecular weight of 35.8 kDa. The molecular weight of the whole fusion protein, including 6His tag and Xpress epitope, was about 68 Kda.

Figure 3:
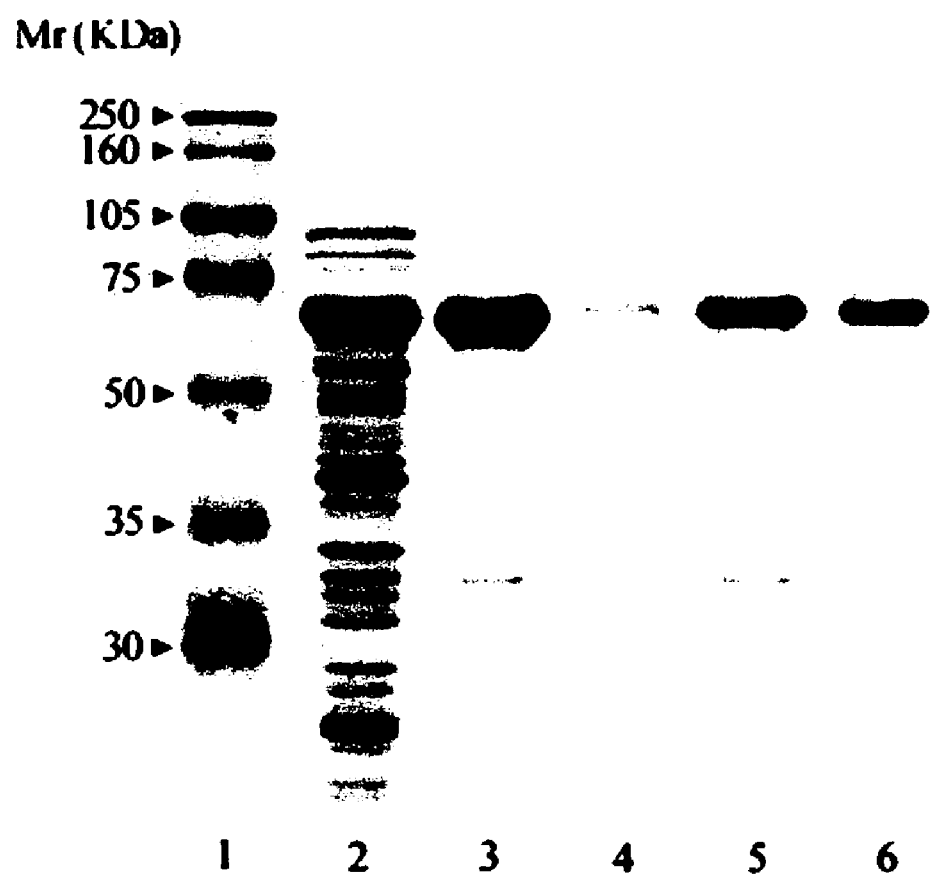
FIG. 3 shows SDS-PAGE analysis of samples from the purification of mA116huFc Ab. Samples were resolved on 10% polyacrylamide gel and stained with Coomassie blue. Lane 1, molecular weight marker; 2, bacterial lysate; 3, solubilized protein fraction; 4, column flow through fraction; 5, 10 and 20 imidazole eluates; 6, final protein preparation.

The mA116huFc Ab was expressed in *E. coli* BL-21 cells and purified by IMAC. SDS-PAGE demonstrated that there was a large amount of protein in the bacterial lysate of molecular weight ~70 kDa, corresponding to the predicted size (68 kDa) of mA116huFc Ab (FIG. 3, Lane 2). After centrifugation of the lysate, and dissolution of the pellet in denaturing agent, many of the proteins were removed from the lysate (FIG. 3, Lane 3). The solubilized protein fraction was incubated with metal affinity resin and loaded to an empty column. After thoroughly washing, the bound fractions were eluted by an imidazole gradient (10 mM to 250 mM) in elution buffer. The 10 and 20 mM imidazole eluates showed a major band at ~70 kDa, accompanied by other weak bands (FIG. 3, Lane 5), whereas, in the eluates of imidazole concentration 50 mM and greater, only the 70 kDa band was present (FIG. 3, Lane 6). In this elution protocol, the expressed protein could be purified to >90%.

Biochemical Characterization

Figure 4:
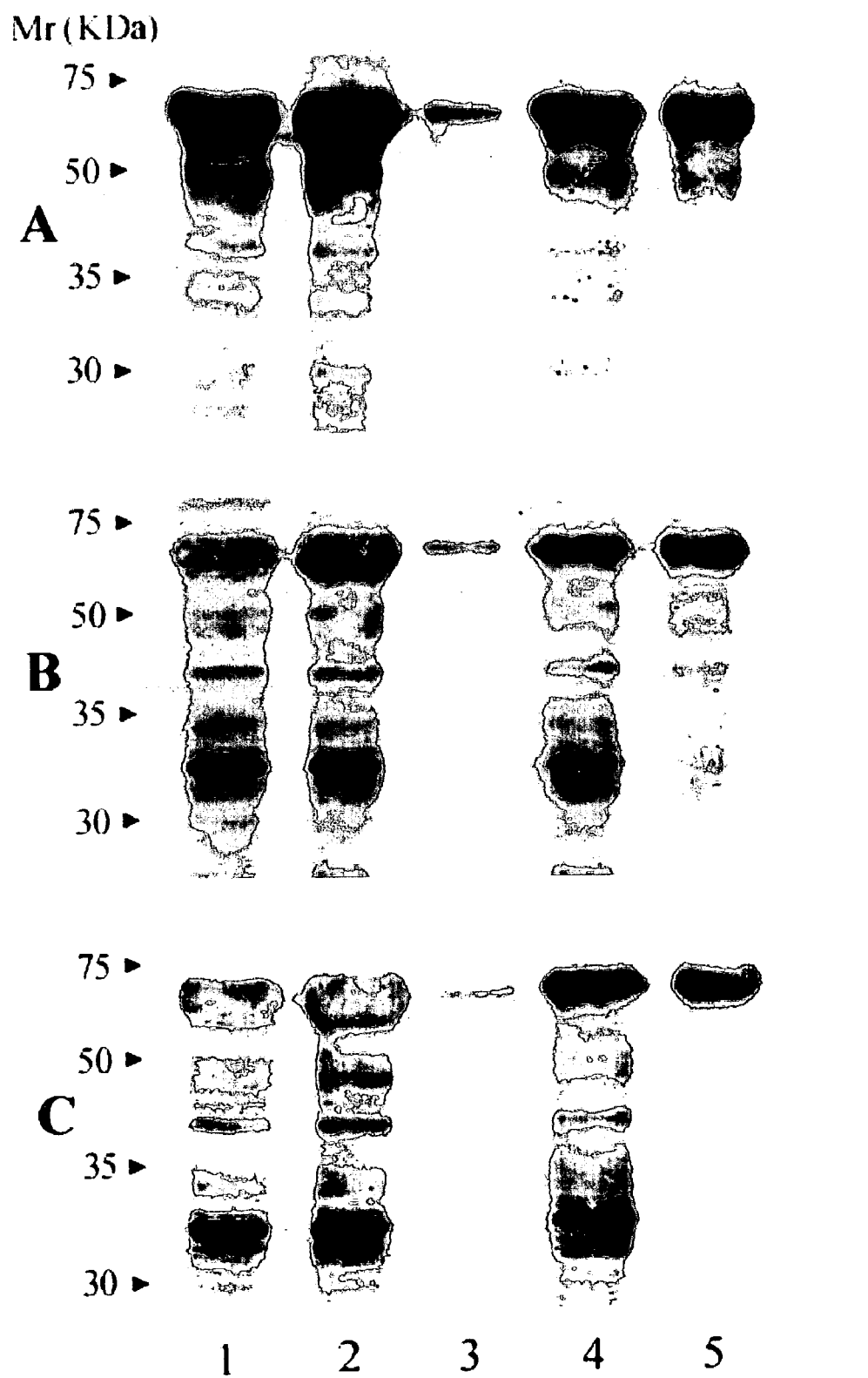
FIG. 4 shows Western blot analysis of samples from the purification of mA116huFc Ab. Samples were resolved by SDS-PAGE, transferred to Immunobilon-P membranes, and probed with (A) HRP-conjugated anti-human Ig, (B) HRP-conjugated Ni—NTA, or (C) anti-Xpress Ab followed by HRP-conjugated anti-mouse Ig. Lane 1, bacterial lysate; 2, solubilized protein fraction; 3, column flow through fraction; 4, 10 and 20 imidazole eluates; 5, final protein preparation.

To confirm the presence of intact, expressed mA116huFc Ab, a series of Western blotting experiments was performed, in which the 70 kDa protein was detected by HRP-anti-human Ig, HRP—Ni—NTA, and anti-Xpress epitope followed by HRP-anti-mouse Ig, respectively. As shown in FIG. 4, the 70 kDa protein was recognized in Western blots by all three of these Abs. The HRP—Ni—NTA and anti-Xpress Abs also detected a 32 kDa fragment in the crude fractions, however, this fragment was eliminated in the purified fraction (FIGS. 4, B and C).

Figure 5:
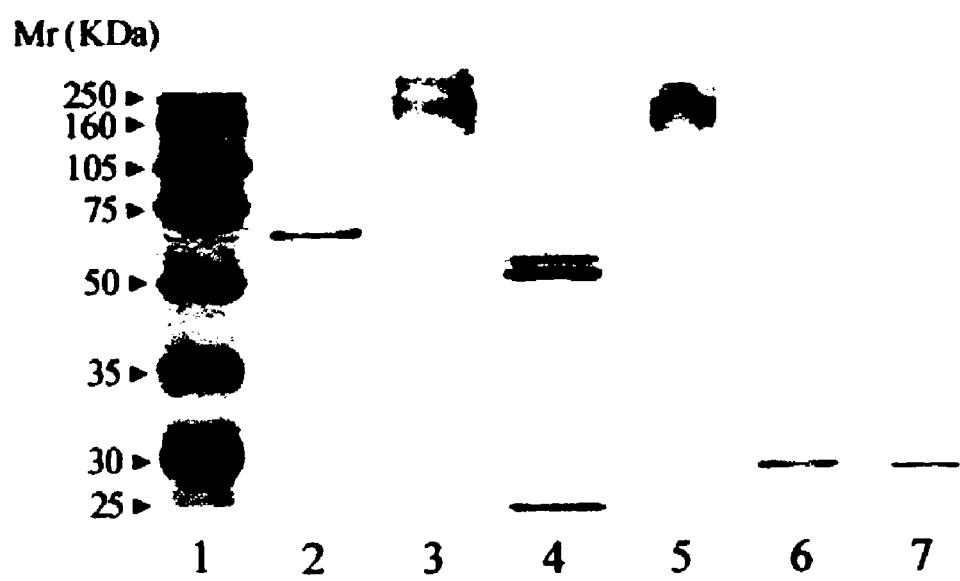
FIG. 5 shows disulfide bond formation assay. Abs were resolved by SDS-PAGE. under reducing or non-reducing conditions and then stained with Commassie blue. Lane 1, molecular weight marker; 2, mA116huFc Ab in reducing condition; 3, mA116huFc Ab in non-reducing condition; 4, 1A4A1 MAb in reducing condition; 5, 1A4A1 MAb in non-reducing condition; 6, mA116 scFv Ab in reducing condition; 7, mA116 scFv Ab in non-reducing condition.

The hinge region of an Ab is responsible for disulfide bond formation between two identical Ab heavy chains. Since mA116huFc Ab contained an intact hinge region, interchain disulfide bond formation was examined by comparing the Ab protein under reducing and non-reducing conditions in SDS-PAGE (FIG. 5). Under reducing conditions (addition of 5% 2-mercaptoethanol), 1A4A1 MAb appeared as two bands, of molecular weight 50 kDa and 25 kDa, representing heavy chain and light chain, respectively (FIG. 5, Lane 4). Under non-reducing conditions, 1A4A1 Ab appeared as high molecular weight aggregates (FIG. 5, Lane 5). Under reducing conditions, mA116huFc Ab migrated as one band of molecular weight ~70 kDa and, under non-reducing conditions, as a high molecular weight aggregate (FIG. 5, Lane 2 and 3). On the other hand, mA116 scFv migrated as only one band of molecular weight ~30 kDa under both reducing and non-reducing conditions (FIG. 5, Lane 6 and 7).

Binding Properties to VEE Antigen

Figure 6A:
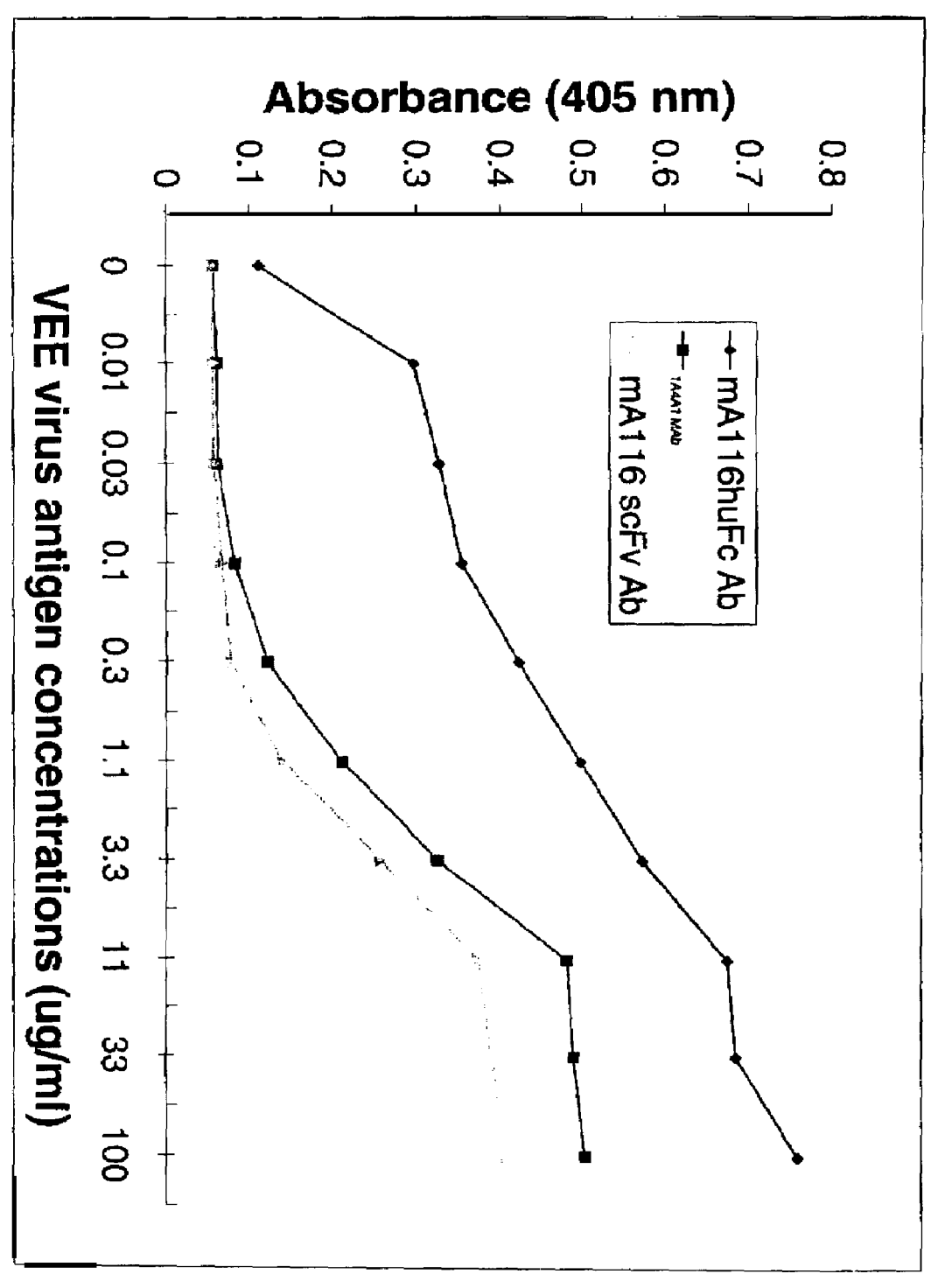
Figure 6B:
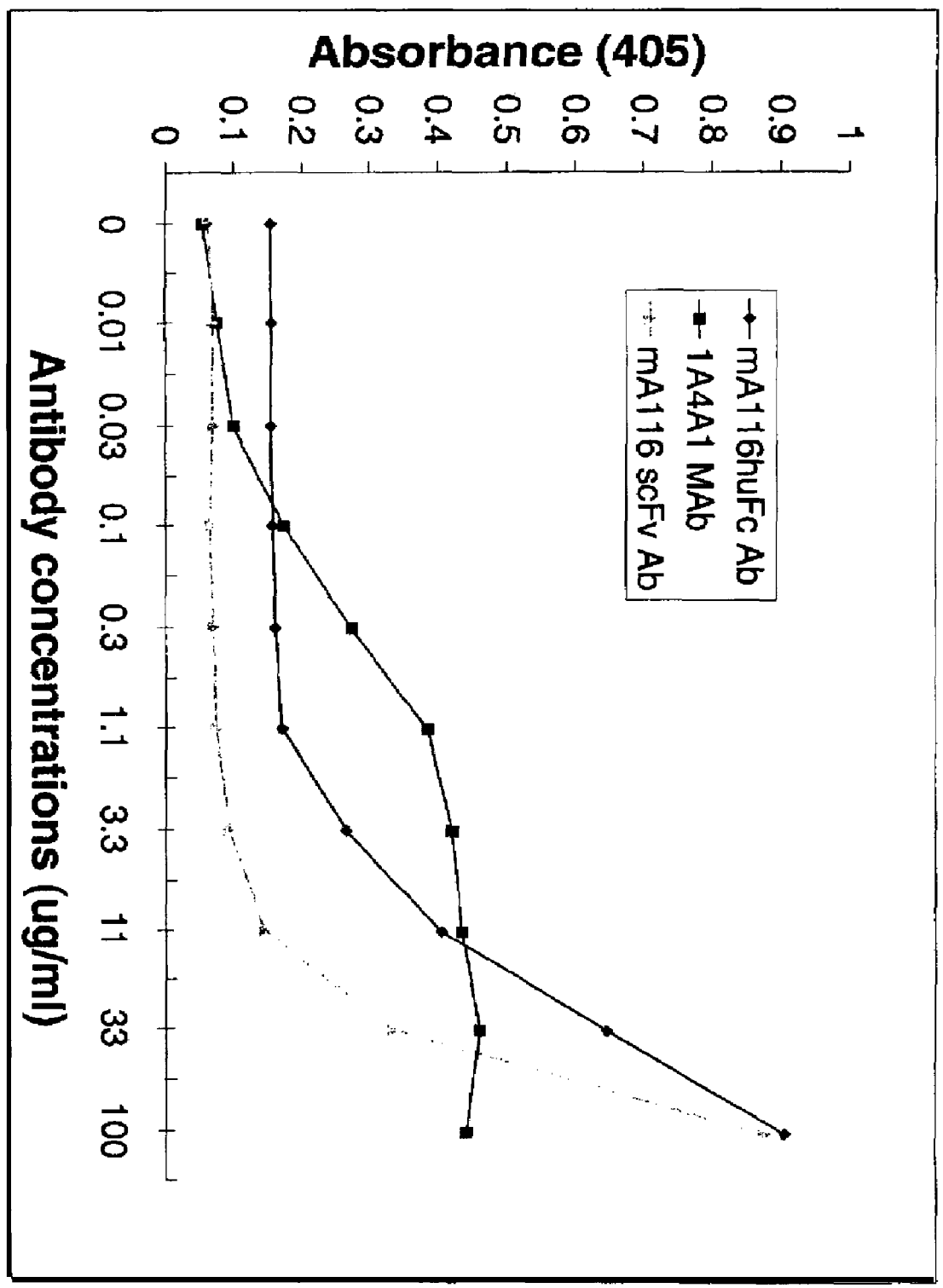
FIG. 6 shows VEE antigen binding assay by ELISA. A. Various concentrations of Abs were added to 96-well plate coated with 10 μg/ml of VEE. B. 10 μg/ml of Abs were added to a 96-well plate coated with various concentrations of VEE. Binding was detected with HRP-conjugated anti-human Ig, anti-mouse Ig, and anti-E-tag Ab, followed by ABTS solution.

The immunoreactivity of mA116huFc Ab to VEE antigen was examined by ELISA. When the plates were coated with a fixed concentration of inactivated VEE (10 µg/ml), mA116huFc Ab bound to VEE in a dose-dependent manner, similar to the binding to VEE of parental 1A4A1 MAb and mA116 scFv Ab (FIG. 6A). An additional ELISA test was performed in which a concentration gradient of VEE was titrated against a fixed concentration of Abs (10 µg/ml). A similar dose-response relationship was observed (FIG. 6B). Furthermore, less than 10 ng/ml VEE could be detected by 10 µg/ml of mA116huFc Ab.

Protein G and C1q Binding

Figure 7:
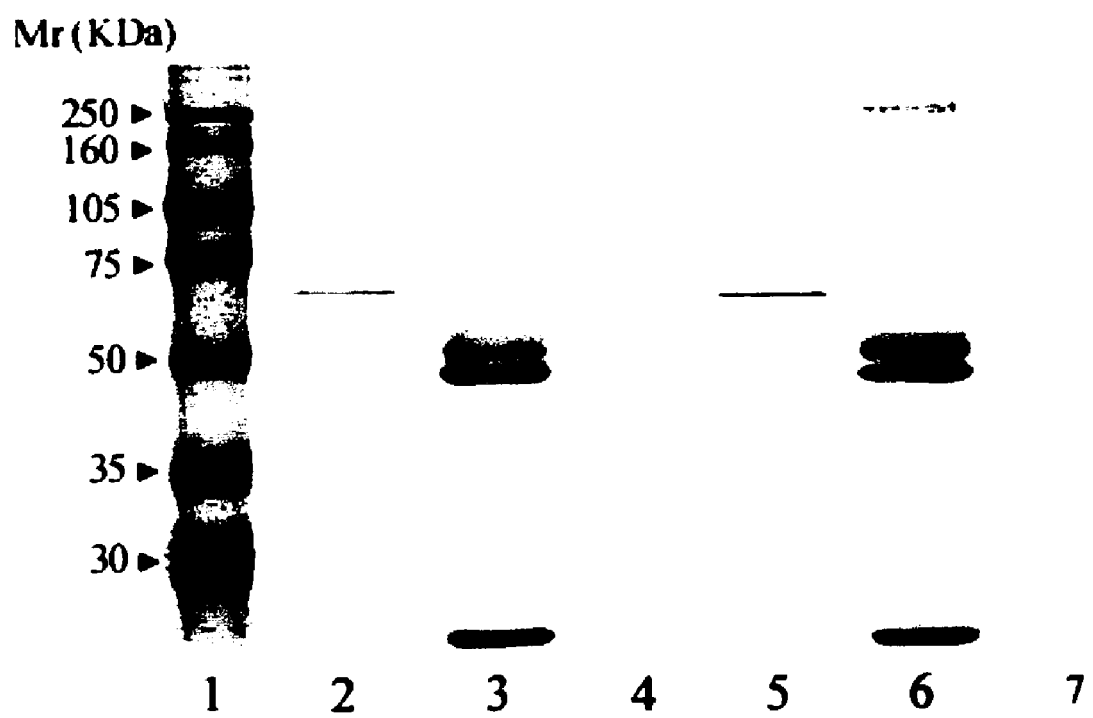
FIG. 7 shows protein G binding assay. Abs were incubated with protein G agarose and precipitated by centrifugation. The pellets were run on SDS-PAGE with Coomassie blue staining. Lane 1, molecular weight marker; 2, mA116huFc Ab only; 3, 1A4A1 MAb only; 4, mA116 scFv Ab only; 5, mA116huFc Ab precipitated by protein G; 6, 1A4A1 MAb precipitated by protein G; 7, mA116 scFv Ab precipitated by protein G.
Figure 8:
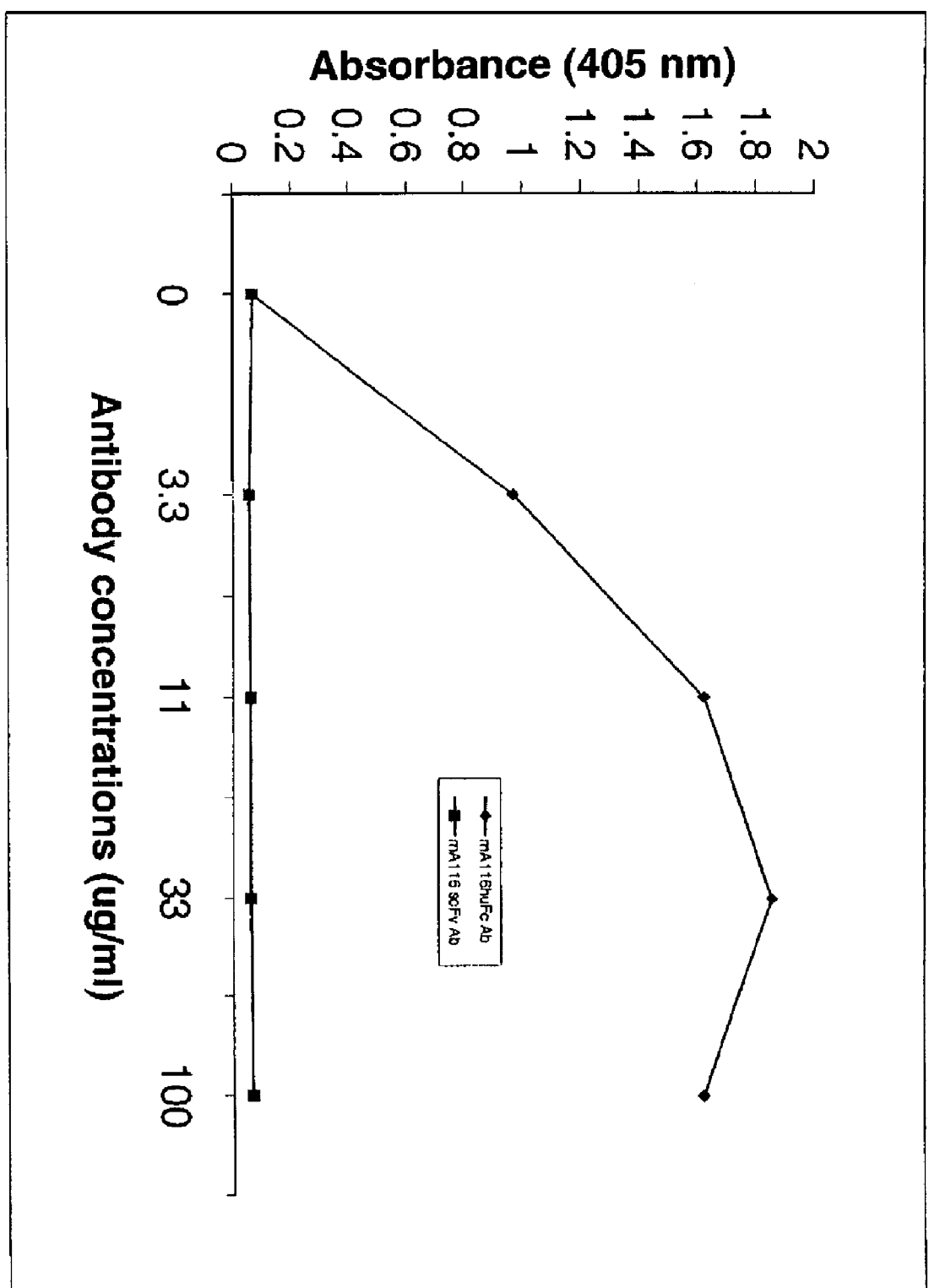
FIG. 8 shows C1q binding assay. The various concentrations of mA116huFc or mA116 scFv Ab were added to strips coated with human C1q protein. Binding was detected with HRP-conjugated anti-human IgG, followed by ABTS solution.

Although 22 residues were missing in the CH1 of mA116huFc Ab, CH2 and CH3 were intact. CH2 and CH3 are believed to be associated with essential features of the constant region of the Abs, such as binding proteins G and A, and effector functions. To determine the affinity of binding of mA116 huFc Ab to the protein G, mA116huFc Ab was incubated with protein G agarose and then, after thorough washing and centrifugation, analyzed by SDS-PAGE. As shown in FIG. 7, the mA116huFc Ab, like its parental 1A4A1 MAb, efficiently bound to protein G agarose, while mA116 scFv Ab did not. To determine whether the mA116huFc Ab could initiate complement activation, one of the important effector functions, an ELISA was performed, in which human C1q was coated on the strips. MA116huFc Ab bound to human C1q in a doze-independent fashion, while mA116 scFv Ab did not bind to human C1q (FIG. 8).

Discussion

The inventors of the present invention have genetically fused anti-VEE mA116 scFv Ab with a human IgG1 heavy chain constant region, in order to confer some human effector functions, and to reduce immunogenicity of the MAb in humans. DNA sequencing confirmed that DNA cloning was successful. The construct, mA116huFc Ab was expressed in E. coli to high levels in the form of insoluble inclusion bodies. The insoluble recombinant mA116huFc Ab was solubilized by denaturing agent, 8 M urea. Inclusion of 6-His tag allowed solubilized recombinant Ab to be purified via IMAC. It has been found that 10 and 20 mM imidazole could minimize nonspecific binding and reduce the amount of contaminating proteins, in spite of some recombinant Ab loss. Accordingly, greater than 90% purity of mA116huFc Ab could be obtained. After purification, arginine was introduced to the recombinant protein solution to direct correct refolding.

The results of Western blot analysis confirmed that the refolded recombinant protein was intact, with a molecular weight of ~70 kDa. A comparison of the SDS-PAGE electrophoretic patterns of mA116huFc Ab, obtained under reducing and non-reducing conditions, was conducted. As expected, mA116huFc Ab migrated as a high molecular weight aggregation under non-reducing conditions, as did the parental 1A4A1 MAb. Under reducing conditions, mA116huFc Ab migrated as one band of molecular weight ~70 kDa, corresponding in size to the monovalent mA116huFc. These results suggested that there was inter-chain disulfide bond formation in the mA116huFc Ab. Included as a control, mA116 scFv Ab migrated as a single ~30 kDa band under both reducing and non-reducing conditions. This finding was as expected as the scFv Ab has no disulfide linkages. However, dimers of scFv Ab fragments have been shown to have a longer biological half life and increased avidity (Adams et al., 1998; Colcher et al., 1998; Long et al., 2000).

The in vitro binding characteristics of mA116huFc Ab to VEE antigen were assayed by ELISA. The mA116huFc Ab exhibited strong binding activity to VEE, indicating that folding was appropriate for the formation of antigen-binding sites. It is worth noting that 10 µg/ml of mA116huFc could detect VEE down to a concentration of less than 10 ng/ml, suggesting the potential utility of mA116huFc Ab for VEE immunodiagnostics applications. The parental 1A4A1 MAb and mA116 scFv Ab showed similar binding activity to VEE, however, a direct comparison of the binding affinities of the three Abs was not possible by ELISA, since each Ab required a different conjugated secondary Ab.

Results of the protein G binding assay indicated that mA116huFc could bind to protein G, thus suggesting that the constant region of mA116huFc Ab was correctly folded. Protein G specifically interacts with CH2 and CH3 constant regions of Ab (Stone et al., 1989). The finding that mA116huFc Ab could bind to protein G suggested that the Fc region must be close in structure to the native profile. The present invention investigated whether the constant region in mA116huFc Ab was folded well enough to activate complement. The classical pathway of complement activation is initiated by the constant region of Ab binding to C1q, a constituent of the first component of complement (Burton, 1985; Hughes-Jones and Garder, 1979). The inventors found that mA116huFc Ab could strongly bind to human C1q in a dose-dependent manner. As expected, mA116 scFv Ab could not bind to C1q due to the lack in Ab structure of the human IgG1 heavy chain constant region. These results indicate that mA116huFc Ab might be active in the recruitment of complement-mediated cell lysis.

All Abs are glycoproteins and are glycosylated at characteristic positions according to their isotype. The IgG molecule has one conserved glycosylation site, at Asn 297, within the CH2 domain of each of its two heavy chains (Sutton and Phillips, 1983). The oligosaccharides are thought to stabilize the molecule and to contribute to the tertiary structure of the constant region, which is very important to such effector functions as complement activation, Fc receptor recognition, and ADCC. Although Asn 457 is available for glycosylation in mA116huFc Ab, bacterial expressions systems are not capable of glycosylating proteins. It has been reported that lack of glycosylation of IgG could affect its binding ability to complement binding capacity (Leatherbarrow et al., 1985; Nose and Wigzell, 1983; Tao and Morrison, 1989). However, the present invention indicates little to no effect of the lack of glycosylation on the ability of mA116huFc to bind to complement.

In summary, a chimeric Ab consisting of the human IgG1 constant region fused to a mouse scFv Ab to VEE has been engineered. This Ab was shown to be a disulfide-linked homodimer, with demonstrated retention of antigen-binding affinity to VEE antigen. In addition, this Ab was shown to possess some human Ig G1 Fc domain functions, such as the ability to bind protein G and human C1q complement. From these findings, it was concluded that this Ab was in a native, functionally active form. The present invention forms the basis for further investigation to characterize mA116huFc Ab in protection studies.

It is to be understood that the embodiments and variations shown and described herein are merely illustrative of the principles of this invention and that various modifications may be implemented by those skilled in the art without departing from the scope and spirit of the invention.

What is claimed is:

1. A recombinant fusion protein molecule comprising two identical chains, each chain comprising a human IgG1 heavy chain constant region and a single-chain variable fragment ("scFv") comprising the amino acids 1 to 300 of SEQ ID NO: 2.

2. The recombinant fusion protein molecule of claim 1, wherein each chain is encoded by the nucleotide sequence shown in SEQ ID NO: 1.

3. The recombinant fusion protein molecule of claim 1, wherein each chain comprises the amino acid sequence shown in SEQ ID NO: 2.

4. The recombinant fusion protein molecule of claim 1, which has a molecular weight of ~70 kDa.

5. The recombinant fusion protein molecule of claim 1, which comprises an inter-chain disulfide bond formation between two identical chains.

6. The recombinant fusion protein molecule of claim 1, which has antigen-binding affinity to Venezuelan equine encephalitis virus ("VEE").

7. The recombinant fusion protein molecule of claim 6, wherein 10 µg/ml of said fusion protein molecule can detect VEE at a concentration of less than 10 ng/ml.

8. The recombinant fusion protein molecule of claim 1, which confers human immune effector functions on murine antibodies.

9. The recombinant fusion protein molecule of claim 8, wherein said human immune effector functions include recruitment of complement-mediated cell lysis.

10. The recombinant fusion protein molecule of claim 1, which is in a functionally active form.

11. The recombinant fusion protein molecule of claim 1, which has human IgG1 crystallizable fragment domain functions.

12. The recombinant fusion protein molecule of claim 11, wherein said domain functions include binding to protein G.

13. The recombinant fusion protein molecule of claim 11, wherein said domain functions include binding to human C1q in a dose-dependent manner.

14. A method of VEE immunodiagnosis comprising contacting the recombinant fusion protein molecule of claim 1 with a sample.

15. The recombinant fusion protein molecule of claim 1, wherein the single-chain variable fragment ("scFv") consists of the amino acids 1 to 300 of SEQ ID NO: 2.

* * * * *

SEQUENCE LISTING

<160> NUMBER OF SEQ ID NOS: 2

<210> SEQ ID NO 1
<211> LENGTH: 1869
<212> TYPE: DNA
<213> ORGANISM: mouse hybridome cells and human lymphocytes
<220> FEATURE:
<221> NAME/KEY: CDS
<222> LOCATION: (1)..(1869)
<223> OTHER INFORMATION: scFv from mouse hybridoma cells and human igG
      heavy chain constant region from human lymphocytes

<400> SEQUENCE: 1

```
atg cgg ggt tct cat cat cat cat cat cat ggt atg gct agc atg act      48
Met Arg Gly Ser His His His His His His Gly Met Ala Ser Met Thr
1               5                   10                  15 ggt gga cag caa atg ggt cgg gat ctg tac gac gat gac gat aag gat      96
Gly Gly Gln Gln Met Gly Arg Asp Leu Tyr Asp Asp Asp Asp Lys Asp
            20                  25                  30 cga tgg gga tcc gag ctc gag atc tgc agc tgg tac cat gga att cct     144
Arg Trp Gly Ser Glu Leu Glu Ile Cys Ser Trp Tyr His Gly Ile Pro
        35                  40                  45 tta gtt gtt cct ttc tat gcg gcc cag ccg gcc atg gcc cag gtc caa     192
Leu Val Val Pro Phe Tyr Ala Ala Gln Pro Ala Met Ala Gln Val Gln
50                  55                  60 ctg cag gag tca gga cct gag ctg gtg aag cct ggg gct tca gtg aag     240
Leu Gln Glu Ser Gly Pro Glu Leu Val Lys Pro Gly Ala Ser Val Lys
65                  70                  75                  80 ata tcc tgc aag gcc tct ggc tac acc ttc act gac tac cat gtt cac     288
Ile Ser Cys Lys Ala Ser Gly Tyr Thr Phe Thr Asp Tyr His Val His
                85                  90                  95 tgg gtg aag ggg aag cct gga cag gga ctt gaa tgg att gga atg act     336
Trp Val Lys Gly Lys Pro Gly Gln Gly Leu Glu Trp Ile Gly Met Thr
            100                 105                 110 tat cct gga ttc gat aat act aat tac agt gag act ttc aag ggc aag     384
Tyr Pro Gly Phe Asp Asn Thr Asn Tyr Ser Glu Thr Phe Lys Gly Lys
        115                 120                 125 gcc aca ttg act gta gac aca tcc tcc aac aca gtc tac atg cag ctc     432
Ala Thr Leu Thr Val Asp Thr Ser Ser Asn Thr Val Tyr Met Gln Leu
    130                 135                 140 agc agc ctg aca tct gag gac acc gct gtc tat ttt tgt gca aga ggt     480
Ser Ser Leu Thr Ser Glu Asp Thr Ala Val Tyr Phe Cys Ala Arg Gly
145                 150                 155                 160 gtg ggc ctt gac tac tgg ggc caa ggg acc acg gtc acc gtc tcc tca     528
Val Gly Leu Asp Tyr Trp Gly Gln Gly Thr Thr Val Thr Val Ser Ser
                165                 170                 175 ggt gga ggc ggt tca ggc gga ggt ggc tct ggc ggt ggc gga tcg gac     576
Gly Gly Gly Gly Ser Gly Gly Gly Gly Ser Gly Gly Gly Gly Ser Asp
            180                 185                 190 atc gag ctc act cag tct cca aat tcg ttg tcc aca tca ata gga gac     624
Ile Glu Leu Thr Gln Ser Pro Asn Ser Leu Ser Thr Ser Ile Gly Asp
        195                 200                 205 agg atc aga atc acc tgc aag gcc agt cag gat gtg gat act gct gta     672
Arg Ile Arg Ile Thr Cys Lys Ala Ser Gln Asp Val Asp Thr Ala Val
    210                 215                 220 ggc tgg tat caa cag aga cca ggg caa tct cct aaa cta ctg att ttc     720
Gly Trp Tyr Gln Gln Arg Pro Gly Gln Ser Pro Lys Leu Leu Ile Phe
225                 230                 235                 240 tgg tca tcc acc cgg cac act gga gtc cct gat cgc ttc aca ggc agt     768
Trp Ser Ser Thr Arg His Thr Gly Val Pro Asp Arg Phe Thr Gly Ser
```

-continued

|   |   |   | 245 |   |   |   | 250 |   |   |   | 255 |   |   |   |   |
|---|---|---|---|---|---|---|---|---|---|---|---|---|---|---|---|

```
gga tct ggg aca gat ttc act ctc acc att agc aat gtg cag tct gaa      816
Gly Ser Gly Thr Asp Phe Thr Leu Thr Ile Ser Asn Val Gln Ser Glu
            260                 265                 270 gac ttg gca gat tat ttc tgt cac caa tat agc agc tat cca ttc acg      864
Asp Leu Ala Asp Tyr Phe Cys His Gln Tyr Ser Ser Tyr Pro Phe Thr
            275                 280                 285 ttc ggc tcg ggg aca aag ttg gaa ata aaa cgg gcg gcc gcg ggc tgc      912
Phe Gly Ser Gly Thr Lys Leu Glu Ile Lys Arg Ala Ala Ala Gly Cys
            290                 295                 300 ctg gtc aag gac tac ttc ccc gaa ccg gtg acg gtg tcg tgg aac tca      960
Leu Val Lys Asp Tyr Phe Pro Glu Pro Val Thr Val Ser Trp Asn Ser
305                 310                 315                 320 ggc gcc ctg acc agc ggc gtg cac acc ttc ccg gct gtc cta cag tcc     1008
Gly Ala Leu Thr Ser Gly Val His Thr Phe Pro Ala Val Leu Gln Ser
                325                 330                 335 tca gga ctc tac tcc ctc agc agc gtg gtg acc gtg ccc tcc agc agc     1056
Ser Gly Leu Tyr Ser Leu Ser Ser Val Val Thr Val Pro Ser Ser Ser
                340                 345                 350 ttg ggc acc cag acc tac atc tgc aac gtg aat cac aag ccc agc aac     1104
Leu Gly Thr Gln Thr Tyr Ile Cys Asn Val Asn His Lys Pro Ser Asn
                355                 360                 365 acc aag gtg gac aag aga gtt gag ccc aaa tct tgt gac aaa act cac     1152
Thr Lys Val Asp Lys Arg Val Glu Pro Lys Ser Cys Asp Lys Thr His
    370                 375                 380 aca tgc cca ccg tgc cca gca cct gaa ctc ctg ggg gga ccg tca gtc     1200
Thr Cys Pro Pro Cys Pro Ala Pro Glu Leu Leu Gly Gly Pro Ser Val
385                 390                 395                 400 ttc ctc ttc ccc cca aaa ccc aag gac acc ctc atg atc tcc cgg acc     1248
Phe Leu Phe Pro Pro Lys Pro Lys Asp Thr Leu Met Ile Ser Arg Thr
                405                 410                 415 cct gag gtc aca tgc gtg gtg gtg gac gtg agc cac gaa gac cct gag     1296
Pro Glu Val Thr Cys Val Val Val Asp Val Ser His Glu Asp Pro Glu
            420                 425                 430 gtc aag ttc aac tgg tac gtg gac ggc gtg gag gtg cat aat gcc aag     1344
Val Lys Phe Asn Trp Tyr Val Asp Gly Val Glu Val His Asn Ala Lys
            435                 440                 445 aca aag ccg cgg gag gag cag tac aac agc acg tac cgt gtg gtc agc     1392
Thr Lys Pro Arg Glu Glu Gln Tyr Asn Ser Thr Tyr Arg Val Val Ser
    450                 455                 460 gtc ctc acc gtc ctg cac cag gac tgg ctg aat ggc aag gag tac aag     1440
Val Leu Thr Val Leu His Gln Asp Trp Leu Asn Gly Lys Glu Tyr Lys
465                 470                 475                 480 tgc aag gtc tcc aac aaa gcc ctc cca gcc ccc atc gag aaa acc atc     1488
Cys Lys Val Ser Asn Lys Ala Leu Pro Ala Pro Ile Glu Lys Thr Ile
                485                 490                 495 tcc aaa gcc aaa ggg cag ccc cga gaa cca cag gtg tac acc ctg ccc     1536
Ser Lys Ala Lys Gly Gln Pro Arg Glu Pro Gln Val Tyr Thr Leu Pro
                500                 505                 510 cca tcc cgg gat gag ctg acc aag aac cag gtc agc ctg acc tgc ctg     1584
Pro Ser Arg Asp Glu Leu Thr Lys Asn Gln Val Ser Leu Thr Cys Leu
                515                 520                 525 gtc aaa ggc ttc tat ccc agc gac atc gcc gtg gag tgg gag agc aat     1632
Val Lys Gly Phe Tyr Pro Ser Asp Ile Ala Val Glu Trp Glu Ser Asn
    530                 535                 540 ggg cag ccg gag aac aac tac aag acc acg cct ccc gtg ctg gac tcc     1680
Gly Gln Pro Glu Asn Asn Tyr Lys Thr Thr Pro Pro Val Leu Asp Ser
545                 550                 555                 560
```

```
gac ggc tcc ttc ttc ctc tac agc aag ctc acc gtg gac aag agc agg   1728
Asp Gly Ser Phe Phe Leu Tyr Ser Lys Leu Thr Val Asp Lys Ser Arg
            565                 570                 575 tgg cag cag ggg aac gtc ttc tca tgc tcc gtg atg cat gag gct ctg   1776
Trp Gln Gln Gly Asn Val Phe Ser Cys Ser Val Met His Glu Ala Leu
            580                 585                 590 cac aac cac tac acg cag aaa agc ttg atc cgg ctg cta aca aag ccc   1824
His Asn His Tyr Thr Gln Lys Ser Leu Ile Arg Leu Leu Thr Lys Pro
            595                 600                 605 gaa agg aag ctg agt tgg ctg ctg cca ccg ctg agc aat aac tag       1869
Glu Arg Lys Leu Ser Trp Leu Leu Pro Pro Leu Ser Asn Asn
    610                 615                 620

<210> SEQ ID NO 2
<211> LENGTH: 622
<212> TYPE: PRT
<213> ORGANISM: mouse hybridome cells and human lymphocytes

<400> SEQUENCE: 2

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Leu Glu Ile Cys Ser Trp Tyr His Gly Ile Pro
        35                  40                  45

Leu Val Val Pro Phe Tyr Ala Ala Gln Pro Ala Met Ala Gln Val Gln
    50                  55                  60

Leu Gln Glu Ser Gly Pro Glu Leu Val Lys Pro Gly Ala Ser Val Lys
65                  70                  75                  80

Ile Ser Cys Lys Ala Ser Gly Tyr Thr Phe Thr Asp Tyr His Val His
                85                  90                  95

Trp Val Lys Gly Lys Pro Gly Gln Gly Leu Glu Trp Ile Gly Met Thr
            100                 105                 110

Tyr Pro Gly Phe Asp Asn Thr Asn Tyr Ser Glu Thr Phe Lys Gly Lys
        115                 120                 125

Ala Thr Leu Thr Val Asp Thr Ser Asn Thr Val Tyr Met Gln Leu
    130                 135                 140

Ser Ser Leu Thr Ser Glu Asp Thr Ala Val Tyr Phe Cys Ala Arg Gly
145                 150                 155                 160

Val Gly Leu Asp Tyr Trp Gly Gln Gly Thr Thr Val Thr Val Ser Ser
                165                 170                 175

Gly Gly Gly Gly Ser Gly Gly Gly Gly Ser Gly Gly Gly Gly Ser Asp
            180                 185                 190

Ile Glu Leu Thr Gln Ser Pro Asn Ser Leu Ser Thr Ser Ile Gly Asp
        195                 200                 205

Arg Ile Arg Ile Thr Cys Lys Ala Ser Gln Asp Val Asp Thr Ala Val
    210                 215                 220

Gly Trp Tyr Gln Gln Arg Pro Gly Gln Ser Pro Lys Leu Leu Ile Phe
225                 230                 235                 240

Trp Ser Ser Thr Arg His Thr Gly Val Pro Asp Arg Phe Thr Gly Ser
                245                 250                 255

Gly Ser Gly Thr Asp Phe Thr Leu Thr Ile Ser Asn Val Gln Ser Glu
            260                 265                 270

Asp Leu Ala Asp Tyr Phe Cys His Gln Tyr Ser Ser Tyr Pro Phe Thr
        275                 280                 285
```

-continued

```
Phe Gly Ser Gly Thr Lys Leu Glu Ile Lys Arg Ala Ala Ala Gly Cys
    290                 295                 300

Leu Val Lys Asp Tyr Phe Pro Glu Pro Val Thr Val Ser Trp Asn Ser
305                 310                 315                 320

Gly Ala Leu Thr Ser Gly Val His Thr Phe Pro Ala Val Leu Gln Ser
            325                 330                 335

Ser Gly Leu Tyr Ser Leu Ser Ser Val Val Thr Val Pro Ser Ser Ser
            340                 345                 350

Leu Gly Thr Gln Thr Tyr Ile Cys Asn Val Asn His Lys Pro Ser Asn
            355                 360                 365

Thr Lys Val Asp Lys Arg Val Glu Pro Lys Ser Cys Asp Lys Thr His
    370                 375                 380

Thr Cys Pro Pro Cys Pro Ala Pro Glu Leu Leu Gly Gly Pro Ser Val
385                 390                 395                 400

Phe Leu Phe Pro Pro Lys Pro Lys Asp Thr Leu Met Ile Ser Arg Thr
                405                 410                 415

Pro Glu Val Thr Cys Val Val Val Asp Val Ser His Glu Asp Pro Glu
            420                 425                 430

Val Lys Phe Asn Trp Tyr Val Asp Gly Val Glu Val His Asn Ala Lys
        435                 440                 445

Thr Lys Pro Arg Glu Glu Gln Tyr Asn Ser Thr Tyr Arg Val Val Ser
    450                 455                 460

Val Leu Thr Val Leu His Gln Asp Trp Leu Asn Gly Lys Glu Tyr Lys
465                 470                 475                 480

Cys Lys Val Ser Asn Lys Ala Leu Pro Ala Pro Ile Glu Lys Thr Ile
                485                 490                 495

Ser Lys Ala Lys Gly Gln Pro Arg Glu Pro Gln Val Tyr Thr Leu Pro
            500                 505                 510

Pro Ser Arg Asp Glu Leu Thr Lys Asn Gln Val Ser Leu Thr Cys Leu
            515                 520                 525

Val Lys Gly Phe Tyr Pro Ser Asp Ile Ala Val Glu Trp Glu Ser Asn
    530                 535                 540

Gly Gln Pro Glu Asn Asn Tyr Lys Thr Thr Pro Pro Val Leu Asp Ser
545                 550                 555                 560

Asp Gly Ser Phe Phe Leu Tyr Ser Lys Leu Thr Val Asp Lys Ser Arg
                565                 570                 575

Trp Gln Gln Gly Asn Val Phe Ser Cys Ser Val Met His Glu Ala Leu
            580                 585                 590

His Asn His Tyr Thr Gln Lys Ser Leu Ile Arg Leu Leu Thr Lys Pro
            595                 600                 605

Glu Arg Lys Leu Ser Trp Leu Leu Pro Pro Leu Ser Asn Asn
    610                 615                 620
```